United States Patent [19]

Galzy et al.

[11] Patent Number: 4,610,887

[45] Date of Patent: Sep. 9, 1986

[54] PROCESS FOR CONCENTRATION OF FERMENTED JUICES BY REVERSED OSMOSIS

[75] Inventors: Pierre Galzy, Montpellier; Guy Moulin, St Gely Du Fesc; Richard Dick, Paris; Gérard Mavel, Antony, all of France

[73] Assignee: Institut National de Recherche Chimique Appliquee, Antony, France

[21] Appl. No.: 661,444

[22] Filed: Oct. 16, 1984

[30] Foreign Application Priority Data

Oct. 17, 1983 [FR] France ............................... 83 16452

[51] Int. Cl.$^4$ ............................................. C12G 3/10
[52] U.S. Cl. .................................. 426/490; 426/592; 426/330.4
[58] Field of Search ............... 426/592, 490, 486, 487, 426/488, 424, 425, 386, 330, 330.3, 330.4, 330.5, 11, 15, 16

[56] References Cited

FOREIGN PATENT DOCUMENTS 089893 9/1983 European Pat. Off. .
2286850 of 0000 France .

OTHER PUBLICATIONS

Underkofler, 1954, Industrial Fermentations, vol. 1, Chemical Publishing Co., Inc., New York, pp. 347, 382 and 383.
Weast, 1970, Handbook of Chemistry and Physics, CRC Press, Cleveland Ohio, p. F-68.
Koyama et al., 1982, J. Applied Polymer Sci, 27:2845–2855.
Mehta, 1982, J. Membrane Science 12: 1–26.
Journal of Membrane Science, vol. 12, No. 1, Nov. 1982, pp. 1–26, *tables 1,2,3; p. 3, point 6; Fig. 1*.
Journal of Applied Polymer Science, vol. 27, No. 2, Aug. 1982, pp. 2845–2855, *tables 2,3; Fig. 2; Fig. 12*.
Transactions A.S.M.E., Journal of Engineering for Industry, Serie B, vol. 97, No. 1, Feb. 1975, ASME, New York (US) pp. 220–223, *p. 222, table 1*.

*Primary Examiner*—Raymond N. Jones
*Assistant Examiner*—Carolyn Paden
*Attorney, Agent, or Firm*—Sheridan Neimark; Karl W. Flocks

[57] ABSTRACT

The present invention relates to a process for treating fermented juices by reversed osmosis in particular for increasing concentration thereof in organic substances. The fermented product is treated under a pressure of from 30 to 120 bars and a strong turbulency by passing it through at least one semi-permeable membrane having a high retention rate with respect to organic substances of molecular weights lower than 200.

4 Claims, 1 Drawing Figure

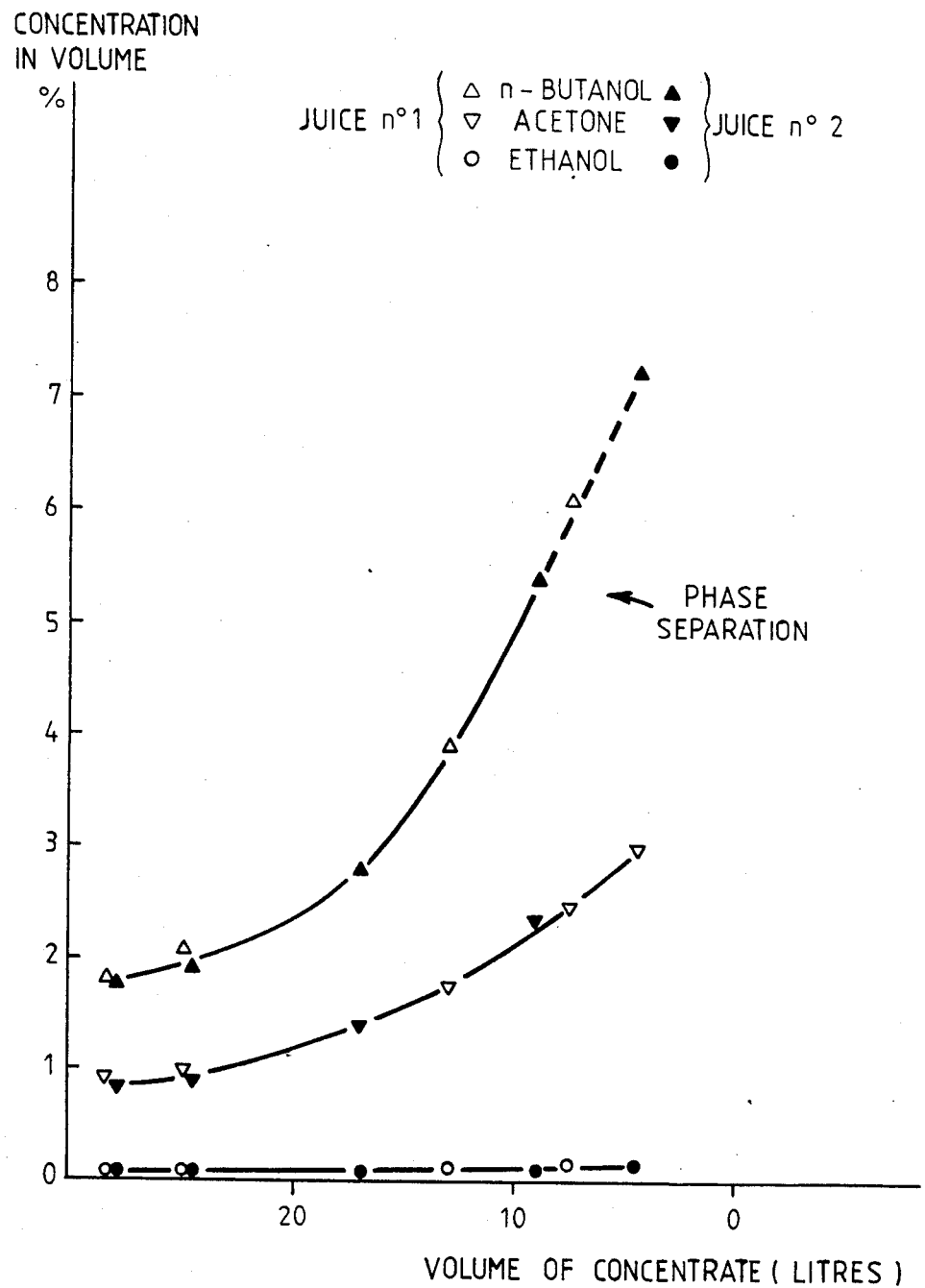

PROCESS FOR CONCENTRATION OF FERMENTED JUICES BY REVERSED OSMOSIS

This invention generally relates to a process for treating fermented juices by reverse osmosis, in particular, for increasing their concentration in organic substances. Such substances resulting from fermentation of sugars whether it be ethanolic, acetonobutylic or other, are mainly substances of a low molecular weight, lower than 200, such as for instance ethanol in case of ethanolic fermentation, and acetone and butanol in case of acetonobutylic fermentation.

The interest of having such a process available resides in the fact that it must be adaptable both to fermented juices to be used as foodstuffs, in this case any fermented beverages as for example wine and beer, and to fermented juices for power producing purposes such as those for the production of fuels.

In the first case, it must be able to increase the alcoholometric titer of the beverages through removal of water while preserving the main elements (aromas, colorants and so on) contained in such beverages, or better while increasing the contents of these elements as permitted by solubility thereof in the medium.

In the second case, it must be able to preconcentrate fermented juices of low contents in power furnishing substances by removal of water to make those techniques profitable, which permit collecting such substances in a pure condition such as by distillation or solvent extraction.

This process must also be carried out by means of any types of apparatuses for reverse osmosis and possibly ultrafiltration.

Recently, membranes with more specific activities can be obtained. Thus, the applicants have developed such membranes which retain under excellent conditions ethanol and alcohols generally (French Pat. No. 2 286 8501). Such membranes permit concentration of alcoholic solutions without however retaining at each passage on the membrane the whole of the alcohols present thereon. Among membranes of this category, one can also cite the membranes PEC 1000 marketed under this designation by the firm TORAY.

The object of this invention is to use such membranes with a view to concentrating fermented juices including fermented beverages such as wine and beer.

Now, these purposes can be reached with the process according to this invention, which is characterized in that it consists of passing the fermented products to be treated under a pressure of from 30 to 120 bars and under a strong turbulency through at least one semipermeable membrane having a high retention rate regarding organic substances of a molecular weight lower than 200, and effecting the number of required passages under the same conditions to obtain a retentate presenting the desired analytic and organoleptic characteristics and in particular, the desired concentrations of organic substances.

The membranes which have proved to be useful in the process according to the invention are those presenting ethanol rejection rates higher than 50% under a pressure of from 50 to 60 bars for an aqueous ethanol solution of 2 to 3%. It is however preferable for the ethanol rejection rates to be comprised between 80 and 99% under the above defined conditions. The ethanol rejection rate is used here as a reference for permitting definition of said membranes. Such rejection rate is itself defined by the relation:

$$\frac{Co - C}{Co} \cdot 100$$

wherein Co designates the ethanol concentration of the retentate and C the ethanol concentration of the permeate.

The applicants have in fact noticed that the conventional reverse osmosis membranes such as those of cellulose acetates intended essentially for water desalting or demineralizing are generally not adequate for the treatment in accordance with this invention, since too high a loss of the organic substances of low molecular weight occurs resulting from passage thereof through the membranes simultaneously with water. The applicants have also observed surprisingly that under the operative conditions in question particularly fragile fermented juices such as wine were not denatured and that their main elements such as aromas, colorants and so on, were preserved whereas one could expect some degree of denaturation owing to the fragility itself of such juices, under certain conditions in particular high pressures.

As an example of membranes applicable according to the invention there can be cited among others those described in French Pat. No. 2 286 850 which are based on a methylolated reticulated derivative of an acrylamide polymer.

Practically, for better efficiency the membranes are moreover selected so as to meet the technological requirements usually encountered in such a type of process, i.e. high compacting strength, the highest possible and constant filtration speed, as high as possible a longevity, cleaning easiness, resistance to micro-organisms, sterilizability.

The process in accordance with this invention can be carried out in various different apparatuses i.e. a system with tubular membranes, a series of modules with planar superimposed or juxtaposed membranes, a module with hollow fibers. It can also be carried out continuously or discontinuously.

In case of fermented beverages the process according to this invention results in a retentate (for example, concentrated wine) which can be treated by any conventional process required for its clarification, removal of tartar depositions and generally, for a preparation for the marketing thereof without any discomfort or risk to the consumer. In case of the wine for example, the concentration causes insolubilization and precipitation of potassium bitartrate and calcium tartrate; therefore, it appears suitable either to treat the wine by cooling, or to maintain it a sufficiently long time so that this phenomenon occurs spontaneously.

The patents which mention the use of reverse osmosis for treating wines exclusively relate to the problems of deacidification or detartaring of wine or the problems of dealcoholization thereof. In the latter case, it is a matter of allowing for passage through the membranes of a permeate having an ethanol content higher than, or at least equal to, that of the retentate and then of lowering the ethanol content of the retentate by adding water thereto.

The process according to this invention on the other hand leads to a permeate having an alcohol content much lower than that of the retentate; it can at most titer 2° to 3°. Moreover, the permeate contains a low proportion of higher alcohols and esters. Direct distillation can be contemplated. However, it might be interesting to retreat the permeate through reverse osmosis so as to increase the alcoholometric titer up to 12° or even 14°. This operation may permit either a simple concentration before distillation or the obtaining of an alcoholic solution that may constitute a basic raw material for a beverage of the bitters type or any other use.

The process according to the invention can be applied to any fermented products without any clear modification of the physico-chemical balance. The advantages of this process as compared to the processes usually utilized for example for increasing the alcoholometric degree of wine such as cryoconcentration, hot concentration of grape musts during the vintage, the addition of concentrates prepared from $SO_2$ mutated are mainly the following: greater flexibility of use related to the possibility of selecting the appropriate time for realizing the treatment; smaller risk of denaturation for the treated products; lower investment and paying off costs owing to the short period of utilization of the equipment, implementing known processes during the harvest, whereas this process can be applied at will after the harvest.

In certain cases the concentration of the fermented beverage may have the single purpose of reducing its water contents so as to decrease transportation costs, with the removed volume of water being added again to the concentrate near the place of consumption.

In case of fermented juices for production of organic solvents such as acetone and butanol for example, the process according to this invention leads to a product having a content of organic solvents much higher than that of the initial juice collected from the fermenter output.

Due to the low energetic consumption of the reversed osmosis the process according to this invention enables to reduce the conventional purification methods for such juices as distillation or solvent extraction.

When the fermented juice contains particles in suspension or macromolecules in solution it might be useful to separate such substances from the juice through decantation, centrifugation, microfiltration or ultra-filtration, or any other process before supplying it into the reverse osmosis module. Due to this, the plugging up of the membranes is reduced and they are washed less frequently. Conversely, it might be useful to separate such substances after feeding fermented juice into the reverse osmosis module. In this case, conventional methods may facilitate precipitation of particles in suspension such as tartrates or of macromolecules in solution.

The number of times the bermented juice should conveniently pass over the membranes depends on the contents of the organic compounds that one desires to obtain.

When the solubility of the organic compounds in the aqueous medium is limited two possibilities exist:
 interrupting the concentration step before reaching phase separation,
 continuing the concentration step after the phase separation.

The separation of the juice into two distinct phases one of which contains more organic compounds than water, whereas the other contains more water than organic compounds may have practical interest. As a matter of fact, the organic compound rich phase is generally less dense than the aqueous and can be separated therefrom by decantation, centrifugation or any other method. This difference in density also prevents contact of the membrane with the organic compounds rich phase thereby to permit continuation of the concentration step. The volume reduction of the aqueous phase to the benefit of the organic phase is compensated for by continuous supply of fermented juice.

The following Examples are given in an illustrative and not at all limitative manner. The Examples in series A relate to wine and those of series B to other fermented juices; it is to be noted that the obtained results are transferable to any liquid containing ethanol and the concentration of which is desired. As can be seen from the results other constituents are also concentrated, and some of them without any loss; therefore the number of passages of the juice over the membrane will in particular be adapted depending on the nature of such juice (wine, beer, cider or any other) and the desired contents of organic substances. Obviously, one has also to take into account legal limitations which vary depending on the product and depending on the country where the transformation occurs.

EXAMPLE I A

A red wine titering at 9°7 not containing any preservative is treated by successive passages over a selective membrane prepared according to the above mentioned Pat. No. 2 286 850.

The membrane used to this end presents the following characteristics in reference to an aqueous solution at 2% (by weight) of ethanol: at 60 bars; flow rate: 160 $l/m^2$- day; ethanol rejection rate: 87.6 % as measured at 25° C. on a planar reversed osmosis module (model LAB 20-DDS).

The treatment of the wine is effected at 80 bars on the same planar reversed osmosis module provided with 0.23 $m^2$ of membrane. The alcoholometric degree is brought to 11°7, corresponding to the legal increase of the alcoholometric titer in France.

The following Table 1 mentions the respective values of the volume and alcoholometric degrees of the initial wine, of its permeate and its retentate as well as the distribution rate of ethanol in the permeate and retentate.

The obtained wine does not present any significant variation of pH, of volatile acidity, of the free and combined $SO_2$, of the methanol, of the higher alcohols, of the aldehydes, of the esters, as shown by the results contained in Table 1. There can be noted a slight increase in the densimetric extract of the fixed acidity and the coloring intensity. At the fixed acidity, the contents of lactic and succinic acids clearly increase. Tartric acid presents a concentration equivalent to the starting one, but solubility of the bitartrate decreases due to the higher ethanol concentration; there results a significant precipitation of tartar which quickly brings the concentrations of tartric acid to a level close to that noted at the beginning. The conventional treatments by cooling have been applied to a portion of the so treated wine, for accelerating precipitation of tartar and improving the quality of the product. After such treatment which consisted of keeping the wine at 4° C. for one month, the characteristics of the wine have on the whole little varied save for tartaric acid which decreased, the contents of tartaric acid being lower by about 16% than that of the initial wine (see last column in Table 1). One can also observe the increase in the coloring intensity, the contents of esters and of higher alcohols.

TABLE 1

| CHARACTERISTICS | INITIAL WINE | RETENTATE | PERMEATE | RETENATE after a month at 4° C. |
|---|---|---|---|---|
| Volume (liters) | 21 | 16.4 | 4.6 | |
| Alcoholometric titer | 9° 7 | 11° 7 | 1° 8 | 11° 7 |
| Distribution of the alcohol quantity (%) | 100 | 95.9 | 4.1 | |
| Density 20/20 | 0.9948 | 0.9940 | 0.9975 | 0.9937 |
| Densimetric extract (g/l) | 20.6 | 24.2 | — | 22.4 |
| Reducing sugars (g/l) | 1.2 | 1.3 | traces | 1.8 |
| Reduced densimetric extract (g/l) | 20.4 | 23.9 | — | 21.6 |
| Ratio of alcohol to reduced densimetric extract | 3.77 | 3.86 | — | 4.29 |
| Polyphenol index | 15 | 22 | — | 21.5 |
| Anthocyans (g/l) | 0.146 | 0.182 | — | 0.157 |
| Ratio of folin index to anthocyans | 102 | 120 | — | 137 |
| Total acidity (g/l): | | | | |
| in | 5.90 | 7.08 | traces | 6.65 |
| in sulfuric acid | 3.86 | 4.63 | traces | 4.35 |
| Volatile acidity (g/l) | 0.30 | 0.29 | traces | 0.35 |
| Fixed acidity | 3.56 | 4.34 | traces | 4.00 |
| Free $SO_2$ (g/l) | 0.010 | 0.012 | 0 | 0.012 |
| Total $SO_2$ (g/l) | 0.048 | 0.051 | 0 | 0.051 |
| Sodium (g/l) | 0.004 | 0.008 | 0.003 | 0.008 |
| Potassium (g/l) | 1.070 | 1.180 | 0.031 | 0.950 |
| Hybrides | presence | presence | — | |
| Color (coloring intensity) $D_{520} + D_{420}$ | 3.84 | 4.06 | — | 4.75 |
| pH | 3.41 | 3.41 | 3.50 | 3.38 |
| Malic acid (g/l) | 0.07 | 0.10 | 0 | 0.10 |
| Tartaric acid (g/l) | 3.1 | 3.4 | 0 | 2.6 |
| Citric acid (g/l) | 0.32 | 0.40 | 0 | 0.37 |
| Lactic acid (g/l) | 1.77 | 2.13 | 0.07 | 2.16 |
| Succinic acid (g/l) | 0.61 | 0.75 | <0.05 | 0.69 |
| Aldehydes (mg/l of ethanol) | 96.8 | 77.4 | 5.3 | 34.3 |
| Esters (mg/l of ethyl acetate) | 114.4 | 140.8 | 44 | 162.8 |
| Furfural | absence | absence | absence | absence |
| Methanol (mg/l) | 82.4 | 86.2 | 47.4 | 93.4 |
| Higher alcohols (mg/l) | 75.8 | 62.3 | 6.0 | 85 |
| from which: | | | | |
| Butanol II mg/l | 0.7 | 0.4 | 0.1 | 0.47 |
| Propanol N mg/l | 19.3 | 18.2 | 1.1 | 25 |
| Isopropanol mg/l | 47.7 | 42.2 | 1.7 | 58.3 |
| Butanol N mg/l | 2.8 | 0.8 | 1.5 | 0.45 |
| Isopentanols mg/l | 5.3 | 0.7 | 1.6 | 0.78 |

EXAMPLE II A

The same red wine titering 9°7 has been submitted to nore intensive treatment from the same membrane as in Example I A and under the same conditions, to permit increase in the alcoholic degree to 12°5. Here too, no significant variation was noted regarding pH, volatile acidity, free and combined $SO_2$, aldehydes, esters, methanol and higher alcohols.

The increase in the concentrations of the mineral materials does not seem to be higher than in the preceding case. The coloration is slightly more increased than previously. The concentration in citric, lactic and succinic acids increases slightly more than in the preceding Example but remains within entirely normal ranges of values (Table 2). For previously mentioned reasons, the concentration in tartaric acid does not increase owing to precipitation of the bitartrate. This Example shows that it is possible to increase the alcoholic degree of the wine by 3° without any disadvantage. Higher concentrations in ethanol were possible with identical conclusions in both of the cited examples. After storage of this wine at 4° C. for one month the same type of evolution (see last column in table 2) as in the preceding example was noted.

TABLE 2

| CHARACTERISTICS | INITIAL WINE | RETENTATE | PERMEATE | RETENTATE after a month at 4° C. |
|---|---|---|---|---|
| Volume (liters) | 14.6 | 10.6 | 4 | |
| Alcoholometric titer | 9° 7 | 12° 5 | 1° 9 | 12° 5 |
| Distribution of the alcohol quantity (%) | 100 | 94.6 | 5.4 | |
| Density 20/20 | 0.9948 | 0.9936 | 0.9972 | 0.9930 |
| Densimetric extract (g/l) | 20.6 | 25.5 | — | 24.2 |
| Reducing sugars (g/l) | 1.2 | 1.5 | traces | 1.8 |
| Reduced densimetric extract (g/l) | 20.4 | 25 | — | 23.4 |

TABLE 2-continued

| CHARACTERISTICS | INITIAL WINE | RETENTATE | PERMEATE | RETENTATE after a month at 4° C. |
| --- | --- | --- | --- | --- |
| Ratio of alcohol to reduced densimetric extract | 3.77 | 3.93 | — | 4.22 |
| Polyphenol index | 15 | 22.5 | — | 23 |
| Anthocyans (g/l) | 0.146 | 0.198 | — | 0.165 |
| Ratio of folin index to anthocyans | 102 | 113 | — | 139 |
| Total acidity (g/l): | | | | |
| in tartaric acid | 5.90 | 7.39 | traces | 7.14 |
| in sulfuric acid | 3.86 | 4.83 | traces | 4.67 |
| Volatile acidity (g/l) | 0.30 | 0.34 | traces | 0.36 |
| Fixed acidity | 3.56 | 4.49 | traces | 4.31 |
| Free $SO_2$ (g/l) | 0.010 | 0.012 | 0 | traces |
| Total $SO_2$ (g/l) | 0.048 | 0.051 | 0 | 0.044 |
| Sodium (g/l) | 0.004 | 0.006 | traces | 0.008 |
| Potassium (g/l) | 1.070 | 1.170 | 0.040 | 0.980 |
| Hybrides | presence | presence | — | — |
| Color (coloring intensity) | | | | |
| $D_{520} + D_{420}$ | 3.84 | 4.53 | — | 5.07 |
| pH | 3.41 | 3.39 | 3.39 | 3.38 |
| Malic acid (g/l) | 0.07 | 0.10 | 0 | 0.10 |
| Tartaric acid (g/l) | 3.1 | 3.2 | 0 | 2.6 |
| Citric acid (g/l) | 0.32 | 0.43 | 0 | 0.37 |
| Lactic acid (g/l) | 1.77 | 2.34 | 0.10 | 2.30 |
| Succinic acid (g/l) | 0.61 | 0.81 | <0.05 | 0.76 |
| Aldehydes (mg/l of ethanol) | 96.8 | 84.5 | 5.3 | 47.5 |
| Esters (mg/l of ethyl acetate) | 114.4 | 140.8 | 70.4 | 162.8 |
| Furfural | absence | absence | absence | absence |
| Methanol (mg/l) | 82.4 | 86.5 | 51.3 | 98.4 |
| Higher alcohols (mg/l) | 75.8 | 49.7 | 5.0 | 80 |
| from which: | | | | |
| Butanol II (mg/l) | 0.7 | 0.4 | traces | 0.48 |
| Propanol N (mg/l) | 19.3 | 18.4 | 1.2 | 25 |
| Isopropanol (mg/l) | 47.7 | 29.3 | 2.1 | 54.2 |
| Butanol N (mg/l) | 2.8 | 1.0 | 0.2 | 0.45 |
| Isopentanols (mg/l) | 5.3 | 0.6 | 1.5 | 0.20 |

EXAMPLE III A

A rose wine titering 10°3 was brought by the process according to the invention to 14°1. All the preceding remarks are valid. However, it appears suitable to observe in particular that the increase in the contents of anthocyans transforms the rose wine into a wine of the "coffee" type. The use of the process according to the invention remains possible for the production of the rose type wine but it will be suitable to provide for a particular vinification upstream: very short dwelling time of the juice in contact with the grape skin to avoid too high a content of coloring materials before concentration; possibly, separate preparation of a small quantity of a "white wine from red wine", i.e. of a wine vinified to white wine, from a red type of wine for subsequent blending.

EXAMPLE IV A

A white wine titering 10°6 was brought to 14°5 by the process according to this invention. The analytic modifications are also identical to the preceding cases. The observed concentration in anthocyans causes variation of the nuance. The color does not vary, only the coloring intensity is stronger.

EXAMPLE V A

A red wine titering 10°4 was brought to 13°4 by the present process. The membrane used for this purpose is the membrane of the PEC-1000 type manufactured by TORAY INDUSTRIES INC. (Japan). The characteristics of the membrane in reference to an aqueous solution at 2% (by weight) of ethanol are the following: at 60 bars; flow rate : 105 l/m²-day; ethanol rejection rate: 95% at 25° C. on a planar reversed osmosis module. All the preceding observations remain valid.

EXAMPLE I B

The following Examples relate to the fermented juices for obtaining organic solvents. Such Examples relate to the juice obtained through butanol-acetone fermentation of Jerusalem artichoke. The results obtained are transferable to any other aqueous fermented liquid of which the organic compounds contained therein are to be concentrated.

A juice obtained from butanol-acetone fermentation of Jerusalem artichoke is clarified at its output from the fermenter through flocculation at 80° C. under reflux followed by a centrifugation. The contents by weight of organic solvents in that juice are the following:

| n-butanol | 1.52% |
| --- | --- |
| acetone | 0.75% |
| ethanol | 0.055% |

To prevent bacterial degradation of such solvents the juice is stabilized by addition of 0.15 g of a solution of formol at 30% by liter of juice. Apart from the mentioned organic solvents, this juice contains a low proportion of organic acids:

| acetic acid | 0.1 to 0.3% |
| --- | --- |
| butyric acid | 0.07 to 0.1% | as well as CaSO₄ and macromolecules in solution: lignins, pectins, pigments, and so on.

The membrane used for treating the juice was prepared according to the French Pat. No. 2 286 850. It presents the following characteristics measured at 60 bars and at 26°±2° C. in respect to an aqueous solution with 2% by weight of ethanol: flow rate 305 l/m²-day, ethanol rejection: 87.7%

The treatment of the juice is effected at 80 bars through repeated passages on a planar reversed osmosis module of 0.07 m² of useful membranous surface. When the concentration in organic solvents is about the double precipitation of the macromolecules in solution is observed. To prevent plugging up of the membrane resulting from those precipitations, the membrane is submitted to a washing about every 24 hours. The washing consists of passing over the membrane slightly acidified water for 15 to 20 minutes at the ambient pressure and at 60 bars, then rinsing the module with water.

The following Table 3 shows the respective values of the volume and the concentrations by volume and by weight in solvents of the initial juice, its permeate and its concentrate as obtained at different stages in the treatment. The distribution rate by weight of the three solvents in the permeate and the concentrate is also shown in said Table.

The phase separation occurs as soon as the concentration by weight of n-butanol exceeds 5%. The n-butanol rich phase having a concentration by weight of n-butanol significantly higher than 50% by weight is first in the form of minute droplets. These collect and fuse to form a liquid which is apparent on the surface of the juice because of its lesser density.

directly treated by reversed osmosis without preliminary clarification or addition of bactericide.

Its contents by weight of organic solvents are the following:

| n-butanol | 1.45% |
|---|---|
| acetone | 0.66% |
| ethanol | 0.038% |

The membrane used for treating the juice was prepared under conditions close to those of the membrane in the preceding Example. Its characteristics as measured at 60 bars and at 26°±2° C. in reference to an aqueous solution at 2% by weight of ethanol are the following:

| flow rate: 319 l/m²-day, |
|---|
| ethanol rejection: 91.4%. |

The treatment of the juice is effected as in the preceding Example at 80 bars with the same module provided with the new membrane. The washing of the membranes is effected a little earlier than in the preceding case because of the high contents of suspension materials in the juice. The results obtained appear in Table 4. One can observe therein that due to a higher selectivity of the membrane as compared to that of the preceding Example, the obtained permeate has a lower contents of solvents than the permeate of the preceding Example and that the distribution rate of the solvents in the permeate and the concentrate is more favorable than in the preceding Example.

TABLE 3

RESULTS RELATIVE TO R.O. CONCENTRATION OF FERMENTED JERUSALEM ARTICHOKE JUICE No 1.

| CHARACTERISTICS | Initial juice | After 4 h. of work | | After 24 h. of work | | After 48 h. of work | | After 70 h. of work | | |
|---|---|---|---|---|---|---|---|---|---|---|
| | | | | | | | | Concentrate | | |
| | | Concentrate | Permeate | Concentrate | Permeate | Concentrate | Permeate | Upper Phase | Lower Phase | Perm. |
| Volume (liters) | 28.5 | 25 | 3.5 | 13 | 15.5 | 7.5 | 21.0 | 4 | | 24.5 |
| | | | | | | | | 0.27 | 3.73 | |
| Ethanol concentration | | | | | | | | | | |
| by weight (%) | 0.056 | 0.06 | 0.013 | 0.095 | 0.022 | 0.12 | 0.033 | 0.16 | 0.136 | 0.039 |
| by volume (%) | 0.070 | 0.076 | 0.12 | 0.028 | 0.15 | 0.042 | 0.20 | 0.172 | 0.172 | 0.049 |
| Acetone concentration | | | | | | | | | | |
| by weight (%) | 0.75 | 0.825 | 0.09 | 1.43 | 0.175 | 2.03 | 0.26 | 2.3 | 1.94 | 0.305 |
| by volume (%) | 0.94 | 1.035 | 0.115 | 1.79 | 0.220 | 2.55 | 0.33 | 2.85 | 2.44 | 0.38 |
| n-butanol concentration | | | | | | | | | | |
| by weight (%) | 1.52 | 1.715 | 0.08 | 3.25 | 0.18 | 5.05 | 0.275 | 57.0 | 5.4 | 0.33 |
| by volume (%) | 1.845 | 2.08 | 0.097 | 3.90 | 0.21 | 6.10 | 0.335 | 69.0 | 6.55 | 0.40 |
| Distribution of the ethanol quantity % | 100 | 97 | 3 | 78.2 | 21.8 | 56.1 | 43.9 | 2.8 | 33.9 | 63.3 |
| | | | | | | | | | 36.7 | |
| Distribution of the acetone quantity % | 100 | 98.5 | 1.5 | 87.2 | 12.8 | 73.7 | 26.3 | 4 | 47.5 | 48.5 |
| | | | | | | | | | 51.5 | |
| Distribution of the n-butanol quantity % | 100 | 99.4 | 0.6 | 93.9 | 6.1 | 86.7 | 13.3 | 35.3 | 46.2 | 18.5 |
| | | | | | | | | | 81.5 | |

EXAMPLE II B

A juice obtained by fermentation under the same conditions as used to obtain the juice of Example I B is

TABLE 4

RESULTS RELATIVE TO R.O. CONCENTRATION OF JERUSALEM ARTICHOKE JUICE No 2.

| CHARACTERISTICS | Initial juice | After 4 h. of work | | After 21 h. of work | | After 44 h. of work | | After 68 h. of work | | |
|---|---|---|---|---|---|---|---|---|---|---|
| | | | | | | | | Concentrate | | |
| | | Concentrate | Permeate | Concentrate | Permeate | Concentrate | Permeate | Upper Phase | Lower Phase | Perm. |
| Volume (liters) | 28 | 24.7 | 3.3 | 17 | 11 | 9 | 19 | 4.4 | | 23.6 |
| | | | | | | | | 0.20 | 4.2 | |
| Ethanol concentration | | | | | | | | | | |
| by weight (%) | 0.038 | 0.042 | 0.008 | 0.052 | 0.019 | 0.079 | 0.0235 | 0.125 | 0.109 | |
| by volume (%) | 0.048 | 0.053 | 0.010 | 0.066 | 0.023 | 0.100 | 0.030 | 0.160 | 0.140 | 0.036 |
| Acetone concentration | | | | | | | | | | |
| by weight (%) | 0.66 | 0.735 | 0.045 | 1.12 | 0.066 | 1.89 | 0.088 | 2.60 | 2.35 | 0.136 |
| by volume (%) | 0.83 | 0.92 | 0.057 | 1.40 | 0.083 | 2.37 | 0.111 | 3.30 | 3.00 | 0.170 |
| n-butanol concentration | | | | | | | | | | |
| by weight (%) | 1.45 | 1.52 | 0.032 | 2.25 | 0.048 | 4.40 | 0.065 | 62.0 | 5.90 | 0.104 |
| by volume (%) | 1.78 | 1.86 | 0.039 | 2.80 | 0.059 | 5.40 | 0.079 | 76.0 | 7.25 | 0.127 |
| Distribution of the ethanol quantity % | 100 | 97.5 | 2.5 | 81.6 | 18.4 | 61.2 | 38.8 | 2.2 | 40.7 | 57.1 |
| | | | | | | | | | 42.9 | |
| Distribution of the acetone quantity % | 100 | 99.2 | 0.8 | 96.3 | 3.7 | 91 | 9 | 3.8 | 73.0 | 23.2 |
| | | | | | | | | | 76.8 | |
| Distribution of the n-butanol quantity % | 100 | 99.7 | 0.3 | 98.6 | 1.4 | 97 | 3 | 31.2 | 62.6 | 6.2 |
| | | | | | | | | | 93.8 | |

The absence of clarification of the juice prior to its concentration treatment only exerted a limited influence upon the duration of the operation. The attached figure shows how the contents of organic solvents in the concentrate increases with the decrease in volume of the latter for the juices of the above two Examples.

It will be understood that this invention was only described in a purely explanatory and not at all limitative manner and that any useful modification thereof can be made without departing from its scope.

We claim:

1. A process for treating fermented juices by reverse osmosis to increase the concentration of organic substances, comprising passing the fermented juices at a pressure greater than 60 bars and under strong turbulency through at least one semi-permeable membrane, said fermented juices having a high content above 2% of organic substances of molecular weight lower than 200, said semi-permeable membrane having a retention rate with respect to organic substances of molecular weight lower than 200 expressed as between 80 and 99% for an aqueous ethanol solution of 2-3% under a pressure of between 50 and 60 bars, said semi-permeable membrane further having high strength and chemical resistance with respect to said organic substances of molecular weight lower than 200, whereby substantially no loss of said organic substances of low molecular weight occurs and a retanate is obtained without denaturation of said organic substances, the analytic and organoleptic characteristics of said organic substances being preserved.

2. The process according to claim 1 wherein said fermented juice is wine.

3. A process according to claim 1 wherein said fermented juice is butanol-acetone fermentation juice.

4. A process according to claim 1 wherein said pressure is approximately 80 bars.

* * * * *